United States Patent [19]

Friedman et al.

[11] 4,264,741
[45] Apr. 28, 1981

[54] TILTABLE FERMENTOR

[75] Inventors: Morton R. Friedman, Highland Park, N.J.; Thomas E. Stinnett, Freemansburg, Pa.

[73] Assignee: New Brunswick Scientific Co., Inc., Edison, N.J.

[21] Appl. No.: 45,810

[22] Filed: Jun. 5, 1979

[51] Int. Cl.³ .............................................. C12M 1/10
[52] U.S. Cl. .................................. 435/312; 366/234; 432/157; 435/303; 435/315; 435/316
[58] Field of Search .............. 435/303, 305, 306, 307, 435/308, 311, 312, 315, 316; 366/220, 224, 228, 230, 231, 234; 432/157, 160, 162; 68/140

[56] References Cited

U.S. PATENT DOCUMENTS

| 827,148 | 7/1906 | Gordon | 435/312 X |
|---|---|---|---|
| 2,244,902 | 6/1941 | Stick | 435/316 X |
| 2,575,673 | 11/1951 | Miller | 68/140 X |
| 3,193,460 | 7/1965 | Krabbe et al. | 435/312 X |
| 3,460,810 | 8/1969 | Mueller | 435/316 X |
| 3,676,074 | 7/1972 | Shibayama et al. | 435/312 X |
| 3,905,865 | 9/1975 | McAleer et al. | 435/312 X |

FOREIGN PATENT DOCUMENTS 938250  6/1962  United Kingdom ..................... 435/312

Primary Examiner—Robert J. Warden
Attorney, Agent, or Firm—Blum, Kaplan, Friedman, Silberman & Beran

[57] ABSTRACT

A tiltable fermentor includes a hollow perforated drum rotating within a generally cylindrical jacketed pressure vessel. The drum is cantilever-mounted and supported at one driven end by a shaft for rotation which is indirectly motor driven by means of an adjustable pulley and belt. The other end of the drum has no central bearing but is circumferentially supported by bearing strips affixed to the inner surface of the outer pressure vessel. A hinged headplate on the pressure vessel, swings open to expose the open undriven end of the inner drum, thereby facilitating loading and unloading. The entire fermentor assembly, that is, vessel, drum and drive, is pivotably mounted so that the rotational axis of the drum may be horizontal or tilted about a transverse axis to a 45 degree angle, with the hinged headplate being either up or down. The drum can rotate at any orientation, and the absence of a drum bearing at the undriven end permits rotational operation even when the headplate is swung open. All required services such as air, steam, and water, and instrumentation and controls are provided.

14 Claims, 4 Drawing Figures

TILTABLE FERMENTOR

BACKGROUND OF THE INVENTION

This invention relates generally to a fermentor of the type used in batch fermentation processes and more particularly to a fermentor which opens at one end and is tiltable such that operation may be at either a horizontal or tilted orientation. In the prior art, the concept of a fermentor comprising a single drum rotating about a horizontally oriented longitudinal axis is well known. Similarly, a horizontal basket or drum rotating within an outer fixed cylinder is also well known in the prior art. U.S. Pat. No. 827,148 discloses a fermentor having a single rotating drum which is mounted at an angle from the horizontal such that there is a permanent tilt to the drum. However, a fermentor including a rotating drum or basket which is tiltable about an axis transverse to its longitudinal rotational axis is not heretofore disclosed. A horizontal fermentor desirably has an end opening which facilitates loading and unloading of the vessel. However, a full diameter headplate on a horizontal fermentor is not practical if loading or unloading is contemplated during rotational operation of the fermentor. Also, when the fermentor is horizontal, a full view of the operational process is not available by opening the full diameter headplate for the obvious reason that the contained materials will spill from the vessel.

What is needed is a fermentor which enables simple loading and unloading of the chamber and is operable in either a tilted or horizontal condition. Further, it is desirable that the fermentor permit operation with the end plate fully open so that the internal process may be observed.

SUMMARY OF THE INVENTION

Generally speaking, in accordance with the invention, a tiltable fermentor especially suitable for loading, unloading, and observation of the operational processes is provided. The tiltable fermentor of this invention includes a hollow perforated drum rotating within a generally cylindrical, jacketed pressure vessel. The drum is cantilevered and supported at one driven end by a shaft for rotation about the longitudinal axis of the drum. The shaft is indirectly motor driven by means of an adjustable pulley and belt. The other end of the drum has no central bearing but is circumferentially supported by bearing strips affixed to the inner surface of the outer vessel. A helical baffle is located within the inner drum for rotation therewith and to facilitate agitation of the substrate and emptying of the vessel. A flat headplate on the pressure vessel swings open on hinges to expose the open undriven end of the inner drum thereby simplifying loading and unloading.

The entire fermentor assembly, that is, the vessel, inner drum and motor drive, is pivotably mounted so that the rotational axis of the drum may be horizontal or tilted about a transverse axis to a 45 degree angle from the horizontal with the hinged headplate being either up or down. The drum can rotate at any orientation and the absence of a drum bearing on the headplate permits rotational operation even when the headplate is swung open. All necessary services such as air, steam and water, and instrumentation and controls are provided in a complete system so that the entire unit may be internally sterilized and then maintained at proper fermentation temperatures as long as the process requires.

Accordingly, it is an object of this invention to provide an improved fermentor which is tiltable during operation and during loading and unloading.

Another object of this invention is to provide an improved fermentor wherein the inner drum or basket is centrally supported only at one end such that the other end provides easy access to the interior of the basket.

A further object of this invention is to provide an improved fermentor having a full diameter hinged headplate which when opened exposes the open end of the inner drum.

Still another object of this invention is to provide an improved fermentor which includes internal means for agitation and emptying the vessel.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
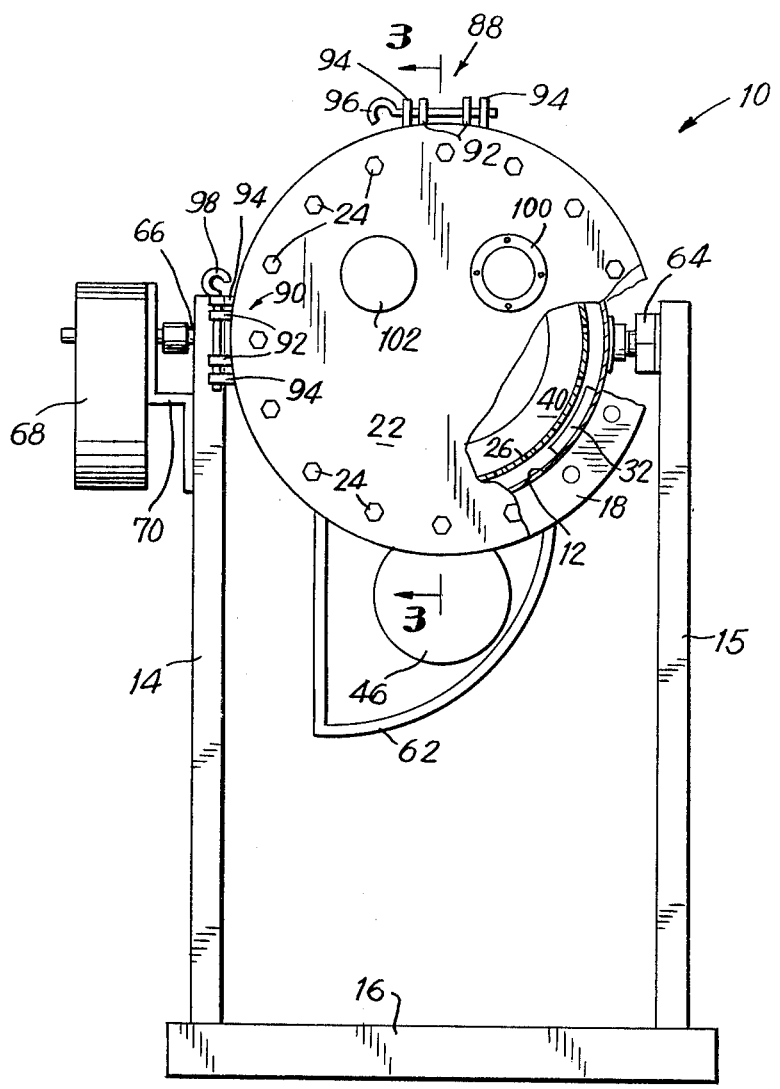
FIG. 1 is a front elevational view of the tiltable fermentor of this invention with a portion cut away.

With reference to the Figures, the tiltable fermentor 10 of this invention includes the fermentor vessel 12 pivotably mounted between vertical supports 14, 15 which connect to a horizontal base 16. The vessel 12 is a cylinder having a flange 18 at one end and a sealed bearing assembly 20 at the other end. A circular headplate 22 abuts the flange 18 and is held in position by a plurality of headbolts 24 arranged in a circle. A gasket (not shown) lies between the flange 18 and the headplate 22 such that a hermetic seal is provided when the bolts 24 are tightened. Accordingly, the vessel 12 is a hermetic pressure vessel which when closed withstands internal vacuum and positive pressures. Because biological cultures may be developed within the fermentor 10 of this invention, the external non-rotating vessel 12 is fabricated of stainless steel and all surfaces which can be in contact with the cultures are also fabricated of stainless steel. All interior surfaces are ground and polished in the conventional manner as suits such fermentor applications. Gaskets, O-rings, and seals, not shown in the Figures for the sake of clarity in illustration and because these items are not novel portions of this invention, are made of ethylene propylene.

Figure 3:
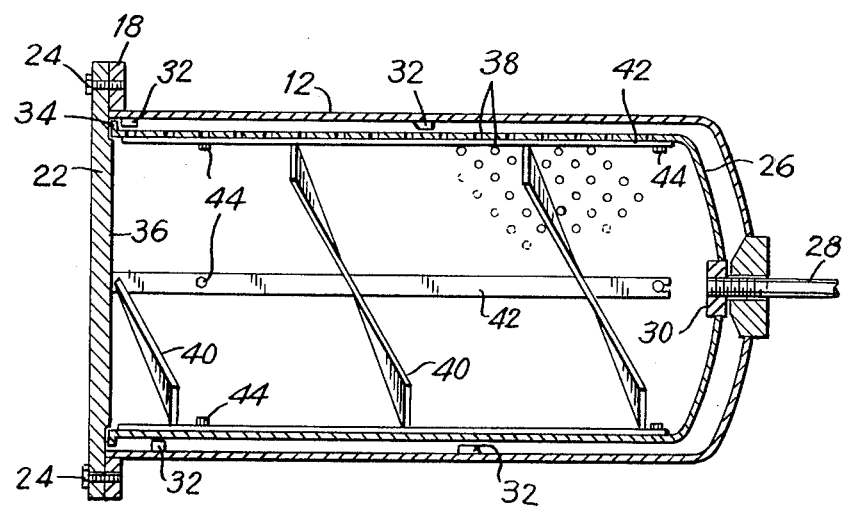
FIG. 3 is a sectional view taken along the line 3—3 of FIG. 1.

A stainless steel drum 26 is located concentrically within the outer vessel 12. The inner drum 26 is mounted for rotation on a shaft 28 which passes through the sealed bearing assembly 20 and enters the vessel 12. As best seen in FIG. 3, the inner drum 26 is generally cylindrical with an open end adjacent the headplate 22. The opposite end of the drum 26 is closed and provided with a threaded end fitting 30 which is coaxial with the rotational axis 80 of the drum 26. The drive-shaft 28 threadably engages the end fitting 30 and supports the closed end of the drum 26. The end fitting 30 is internally threaded such that normal rotation of the drive-shaft 28 causes a tightening of the connection between the shaft 28 and fitting 30. When the headplate 22 is removed or swung back in an open position, as discussed more fully hereinafter, the inner drum 26 may be unthreaded from the drive-shaft 28 and removed through the open end of the vessel 12 for cleaning or replacement.

The drum 26 is cantilever mounted from the shaft 28. Additionally, the drum 26 is supported within, and aligned to, the vessel 12 by means of plastic bearing strips 32 affixed to the inner surface of the vessel 12 and having a curvature which provides for a low-friction sliding contact with the drum 26, thereby facilitating easy rotation of the drum 26 within the vessel 12. Bearing strips 32 are spaced circumferentially at 120 degree intervals. Rulon, a non-abrasive reinforced fluorocarbon, and Teflon are examples of plastic materials suitable to serve as the bearing strips 32.

A radial flange 34 around the open end of the inner drum 26 provides rigidity for the open end of the drum 26 and also fits concentrically around a slightly elevated portion 36 on the inside surface of the headplate 22. Thus, the cantilever mounting at the closed end of the drum 26 is relieved of bending stresses by means of the bearing strips 32, and the nesting of the flange 34 on the headplate 22 prevents the escape of solid materials from the inner drum 26. The drum 26 has perforations 38 in its side wall to allow easy transfer of liquid to all portions of the vessel 12.

A helical baffle 40 is connected to the inner side wall of the rotating perforated drum 26 by means of longitudinal strips 42 to which the helical baffle 40 is rigidly attached. The longitudinal strips 42 are rigidly but removably attached by bolts 44 to the inner drum 26. The baffle 40 rotates with the inner drum 26 and aids in agitating the substrate and culture materials which are within the vessel 12. The helical baffle 40 is readily removed by loosening the bolts 44 and removing the baffle structure through the open end of the vessel 12 when the headplate 22 is removed or swung open.

A drive motor 46 drives a pulley 48 through a speed reducer 50, and the pulley 48 connects by means of a belt 54 to a second pulley 52 fixedly attached to the drive-shaft 28. Accordingly, the shaft 28 rotates the inner drum 26 at a speed which is much reduced from the normal rotational rate of the motor 46. The motor 46 and speed reducer 50 are integrally mounted to the external vessel 12 by means of brackets 56. Tension of the belt 54 is adjusted by means of a hinge 58 and adjusting bolts 60 in the conventional manner. The drive-shaft 28 extends from the pulley 52 to the end fitting 30 on the drum 26 through the bearing housing 20 which includes dual rotating mechanical seals and ball-bearings (not shown) on the shaft 28 which are double sealed with sterile condensate lubrication. Thus, the sealed integrity of the entire fermentor 10 of this invention is preserved. The belt guard 62 protects personnel from exposure to the moving drive elements of the fermentor 10.

A trunnion 64 is fixedly attached to the vertical support 15 and pivotably supports the vessel 12 on the one side. A trunnion 66 extends from an actuator 68 to pivotably support the vessel 12 from the opposite side. The actuator 68 is rigidly attached to the vertical support 14 by means of an offset bracket 70. As explained more fully hereinafter, when the actuator 68 operates, the trunnion 66 rotates and tilts the vessel 12 in unison. Note that when the vessel 12 tilts, the inner drum 26, the motor 46, the speed reducer 50, and the intermediate drive including the pulleys 48, 52 and belt 54 rotate in unison with the trunnion 66 and vessel 12. Because of its attachment to the vessel 12 by means of the brackets 56, the motorized drive is no impediment to simple tilting of the fermentor 10 of this invention.

Figure 4:
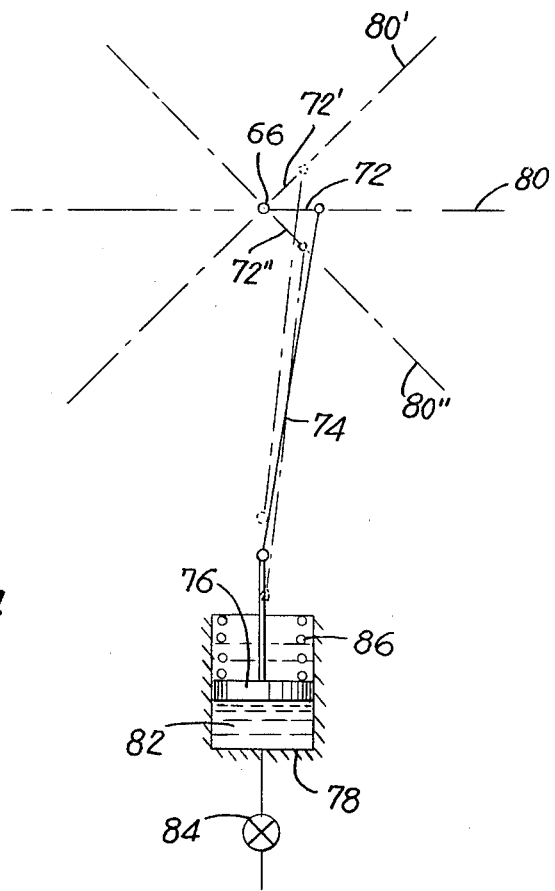
FIG. 4 is a semi-schematic representation of the actuator for the tiltable fermentor of FIG. 1.

In a preferred embodiment of this invention, the actuator 68 comprises a linkage mechanism as illustrated semi-schematcally in FIG. 4. The driving trunnion 66 connects by means of a crank 72 and connecting rod 74 to a piston 76 which reciprocates within a stationary cylinder 78. The actuator is shown (FIG. 4) in the position where the longitudinal axis 80 of the vessel 12 is horizontal. When compressed gas is admitted to the cylinder chamber 82 through the valve 84, the piston 76 is driven against the opposing bias spring 86 such that the crank 72 moves to the position indicated in the drawing by a broken line having the reference numeral 72'. The rigidly attached trunnion 66 rotates in a counterclockwise direction whereby the flanged end 18 of the fermentor 10 of this invention is tilted upward. Similarly, when the compressed gas is released from the chamber 82, the action of the spring 86 causes the piston 76 to move to the inlet end of the chamber 82, whereby the crank moves to the position indicated by the reference numeral 72'', and the vessel 12 tilts with the flanged end 18 downward. Stops (not shown) limit the travel of the piston 76 and restrict tilting to ±45 degrees from the horizontal although the tilting angle need not be limited to this one range. Whereas, a sigle-acting actuator 68 has been illustrated and described, it should be readily understood that in alternative embodiments of this invention, the actuator may be double acting with compressed gases being input to both sides of the piston in turn to accomplish the tilting to any desired position and return of the fermentor 10. Also, springs on both sides of the piston may be used to bias the fermentor 10 to a horizontal position. Mechanical locking devices (not shown) are included to lock the vessel 12 in any position, horizontal or tilted, such that orientation is maintained even in the unforeseen event where compressed gas is lost from the actuator due to a failure in the supply system. Also, pressurized liquid may be used in the actuator 68 as the driving fluid in place of the compressed gas.

Figure 2:
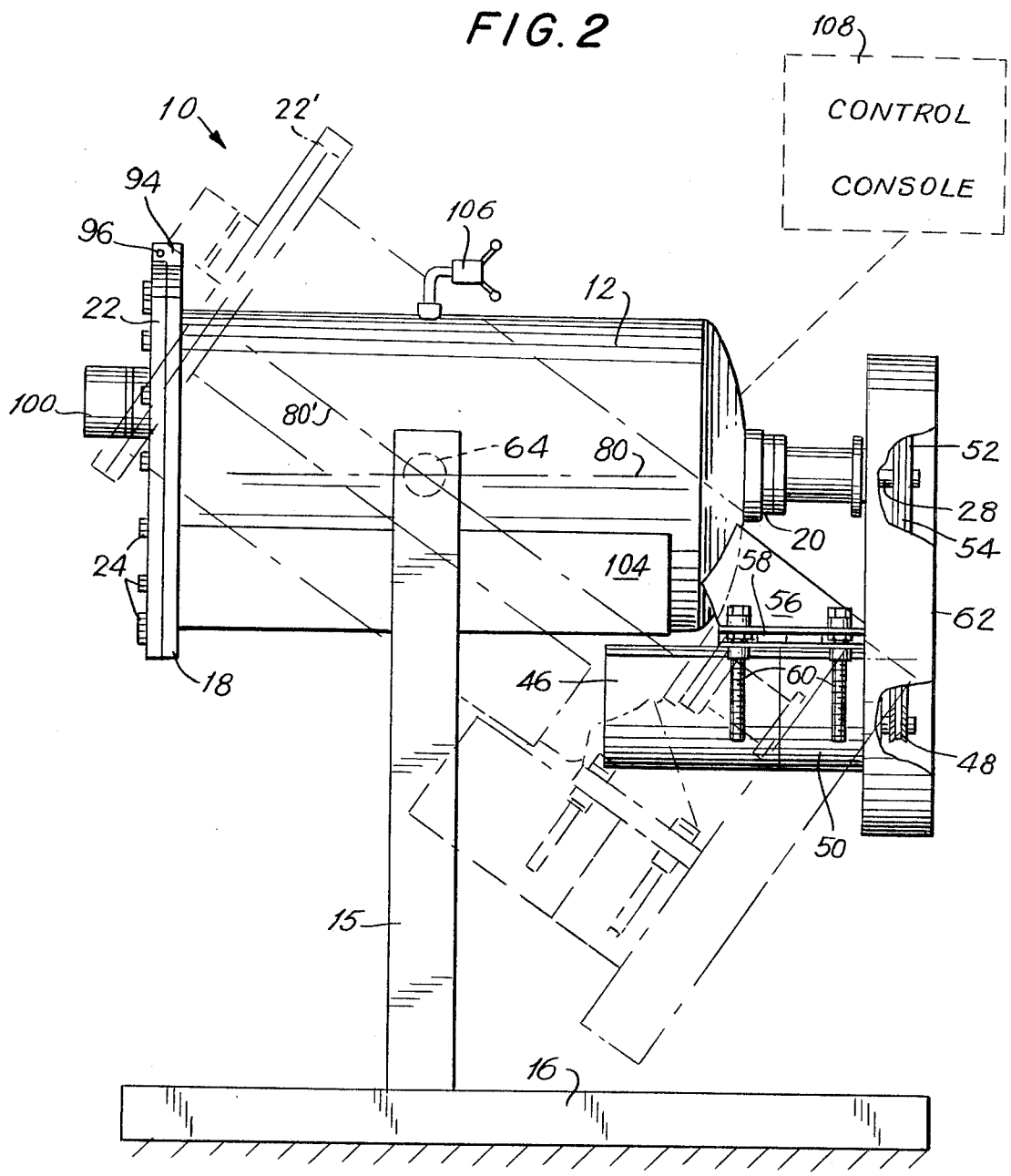
FIG. 2 is a right side view of the fermentor of FIG. 1.

As stated above, the headplate 22 is secured to the vessel 12 by the circle of bolts 24 which pass through the headplate 22 and engage in threaded holes in the flange 18. Additionally, the headplate 22 is held by a horizontal hinge assembly 88 and a vertical hinge assembly 90 which join the headplate 22 to the flange 18. When the bolts 24 are loosened and removed, the headplate 22 remains suspended in position adjacent the flange 18, being supported by the hinge assemblies. Each hinge assembly 88, 90 is comprised of a pair of tabs 92 extending from the headplate 22 and a pair of tabs 94 attached to the edge of the flange 18. Each tab has a hole passing therethrough which is aligned such that a hinge pin 96 passes through the horizontal hinge assembly 88 and a hinge pin 98 passes through the vertical hinge assembly 90. The hinge pins 96, 98 are removable by pulling on the hooked ends. When the hinge pin 96 is removed from the hinge assembly 88, the headplate 22 can swing open horizontally about the hinge assembly 90. When only the hinge pin 98 has been removed, the headplate 22' can swing upward, pivoting on the hinge pin 96 as shown in the broken lines of FIG. 2. Accordingly, there are three ways to open the flanged end of the vessel 12, that is, by swinging the headplate 22 open either horizontally or vertically, or by entirely removing the headplate 22 by removing the bolts 24 and both hinge pins 96, 98.

Although the headplate 22 is removed, the inner drum 26 is supported in the usual manner, as described above, at the shaft end by the shaft 28 and along its length by the plastic bearing strips 32. The inner drum 26 can be rotated while the headplate 22 is open or removed, and the vessel 12 may be tilted, as described above, while the inner drum 26 is rotating and the headplate 22 is open or removed. The headplate 22 may be opened or removed for loading and unloading of substrate, or merely for observation during operation while the flanged end of the vessel 12 is tilted upward. There are no bearings to obstruct access to the inside of the drum 26 and vessel 12 when the headplate 22 has been removed or placed in an open position.

The tiltable fermentor 10 of this invention is fitted with auxiliary appurtenances known in the art. For example, the headplate 22 includes a sight-port 100 which is used for viewing the interior of the vessel 12 and for filling the vessel 12 with liquid. A light source 102 is provided in the headplate 22, and a lower portion of the vessel 12 has an external jacket 104 through which are circulated fluids used in heating and cooling the contents of the vessel 12. Sterilization and temperature control during fermentation are provided by means of the jacket 104. A steam lock port 106 allows for addition of innoculating materials and other materials to the vessel 12 prior to and during operation of the fermentor 10. Instrument ports (not shown) are provided for all required sensors, and ports are provided passing through the pressure vessel 12 for entrance of required services such as air, steam, water, nutrients, and the like. A control console indicated generally in FIG. 2 by the reference numerial 108 includes readouts for all instruments such that the fermentation processes may be monitored, and includes all manual and automatic controls which need be operated in loading, operating, and unloading the fermentor 10 of this invention. A more detailed description of these devices is omitted from this disclosure as they do not constitute a novel portion of this invention.

In a typical use of the fermentor 10 of this invention, the headplate 22 is placed in an open position by pivoting around one hinge pin after the other hinge pin and the head bolts 24 have been removed. The actuator 68 moves the vessel 12 such that the open end is tilted upward. The drum 26 may be rotated by operation of the motor 46 while the pressure vessel 12 and inner drum 26 are being filled, so that mixing action within the fermentor 10 may be observed. Then the headplate 22 is firmly secured by means of the head bolts 24, and the temperature of the materials within the vessel 12 is raised to sterilization temperature by circulation of hot fluid or steam through the jacket 104. During sterilization, the contents of the vessel 12 are mixed by operation of the motor 46. After a pre-determined period at sterilization temperature, the contents of the fermentor 10 are cooled to operating temperature by the circulation of cooling fluids through the jacket 104 and then the chamber is maintained at fermentation temperature and pressure for the desired period of time. When the process has been completed the fermentor 10 is emptied by removal or opening of the headplate 22 while the inner drum 26 is rotated and the vessel 12 is tilted with the open end pointed downwardly. At any time during the operational processes, the vessel 12 may be tilted with the flanged end upward and the headplate 12 may be removed or opened for observation of the action occuring within the chamber 12.

It should be understood that in alternative embodiments of this invention, other materials compatible with fermentation cultures may be used in fabricating the vessel 12 and internal parts. These materials may include plastics and ceramics or metals coated with plastic, ceramic or other metals. Also, it should be readily understood by those skilled in the art that the motor drive and controls may be adapted to provide oscillatory motion to the inner drum about the axis 80 or mixed cycles of rotational and oscillatory motion. Further, the actuator may be controlled to provide cycles of oscillatory motion about the transverse axis through the trunnions whereby the contained materials are sloshed from end to end of the vessel for purposes of mixing and agitation.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A fermentor, comprising:
   an outer cylindrical vessel having an end opening therein;
   a hollow cylindrical drum within said vessel, said drum having an unobstructed end opening therein, said drum opening substantially opposing said opening in said vessel;
   means for imparting relative rotational motion between said drum and said vessel, said openings remaining opposed during said relative motion;
   bearing means located between said vessel and said drum for contraining the position of, and supporting said drum within said vessel, said bearing means not obstructing said opposed openings;
   a headplate for closing said end opening in said vessel;
   reversible means for retaining said headplate adjacent to and closing said vessel end opening;
   means for tilting said vessel and said drum about an axis through said vessel and transverse to the axis of said relative rotational motion, whereby said openings may face upward, downward or horizontally and when said headplate is not closing said vessel opening, unobstructed access to the interior of said drum through said opening is always provided.

2. The fermentor as claimed in claim 1 wherein said means for imparting relative motion between said drum and said vessel is fixedly attached to said vessel, whereby said vessel and said means for imparting relative motion tilt in unison.

3. A fermetor as claimed in claim 2 wherein said relative motion between said drum and said vessel is produced by rotation of said hollow drum.

4. A fermentor as claimed in claim 3 wherein said vessel opening is at one end of said vessel, said means for imparting relative motion being connected to one end of said hollow drum, said connected end of said hollow drum being opposite said opening in said drum.

5. A fermentor as claimed in claim 4 wherein said means for imparting relative motion includes a motor.

6. A fermentor as claimed in claim 4 wherein said bearing means are comprised of low-friction strips affixed to the inner surface of said vessel, said strips being in sliding engagement with the outer wall surface of said hollow drum.

7. A fermentor as claimed in claim 6 wherein said side wall of said hollow drum is perforated whereby liquids in said vessel are readily distributed.

8. A fermentor as claimed in claim 7 and further comprising an agitator within said hollow drum and moving therewith.

9. A fermentor as claimed in claim 8 wherein said agitator is a helical baffle connected to the inner wall of said drum.

10. A fermentor as claimed in claim 6 wherein said low-friction strips are composed of a non-abrasive reinforced fluorocarbon.

11. A fermentor as claimed in claim 2 wherein said means for tilting includes a pair of trunnions, said trunnions engaging opposite sides of said vessel, the axis of tilting between said trunnions being horizontal.

12. A fermentor as claimed in claim 11 wherein said means for tilting further includes means for rotating at least one of said trunnions whereby said vessel is tilted.

13. A fermentor as claimed in claim 12 wherein said means for rotating said at least one trunnion includes a piston connected to a linkage mechanism, said at least one rotated trunnion being a pin in said linkage mechanism.

14. A fermentor as claimed in claim 1 or 12, and further comprising a jacket affixed to said vessel, said jacket being adapted for circulation of temperature controlled fluids therein, said vessel and said jacket being in a heat transfer relationship, whereby the contents of said vessel may be thermally affected by the temperature of said fluids circulated in said jacket.

* * * * *